United States Patent [19]

Carro et al.

[11] Patent Number: 4,522,922
[45] Date of Patent: Jun. 11, 1985

[54] SOLUBLE ASSAY

[76] Inventors: José Carro, 2850 SW. 122 Ave., Miami, Fla. 33175; Frank de Velasco, 10945 SW. 75 Ct., Miami, Fla. 33156

[21] Appl. No.: 368,961

[22] Filed: Apr. 16, 1982

[51] Int. Cl.³ ............... G01N 33/50; G01N 33/54; G01N 33/60
[52] U.S. Cl. ............... 436/500; 436/501; 436/504; 436/536; 436/538; 436/539; 436/540; 436/542; 436/804; 436/808; 436/809; 436/811; 436/817; 436/820; 436/828; 435/4; 435/7; 206/569
[58] Field of Search ............ 424/1, 1.5; 23/230 B; 436/536–540, 542, 541, 500–504, 804, 819, 808–809, 811, 815, 817, 820, 828, 4, 7, 5, 810; 435/4, 7; 206/569

[56] References Cited

U.S. PATENT DOCUMENTS

| | | | |
|---|---|---|---|
| 3,555,143 | 1/1971 | Axen et al. | 424/1 |
| 3,935,074 | 1/1976 | Rubenstein et al. | 436/537 |
| 4,034,474 | 7/1977 | Miles | 436/518 |
| 4,088,746 | 5/1978 | Blakemore et al. | 424/1 |
| 4,098,876 | 7/1978 | Piasio et al. | 424/1 |
| 4,130,462 | 12/1978 | Rubenstein et al. | 436/537 |
| 4,199,559 | 4/1980 | Ullman et al. | 424/8 |
| 4,244,940 | 1/1981 | Jeong et al. | 424/1 |
| 4,248,965 | 2/1981 | Mochida et al. | 435/7 |
| 4,278,652 | 7/1981 | Niemann et al. | |
| 4,281,061 | 7/1981 | Zuk et al. | 436/537 |
| 4,297,494 | 10/1981 | Groman et al. | 544/267 |
| 4,298,592 | 11/1981 | Lin et al. | 436/540 |
| 4,343,896 | 8/1982 | Wolters et al. | 435/7 |
| 4,353,982 | 10/1982 | Gomez et al. | 435/7 |

OTHER PUBLICATIONS

J. Immunological Methods, vol. 45, pp. 255–278, (1981), Hunter, W. M. and Budd, P. S.
Immunochemistry, vol. 15, pp. 71–76, (1978), Rodbard, D. and Feldman, Y.

Primary Examiner—Ben R. Padgett
Assistant Examiner—M. Morkowitz

[57] ABSTRACT

Ligand having at least two determinant or binding sites is contacted with a labeled first binder, an unlabeled second binder different than the first binder and a precipitating binder specific for the second binder, with such contacting precipitating a complex of the ligand and the first and second binders to thereby separate bound labeled binder from unbound labeled binder. The bound and/or unbound labeled binder is determined as a measure of the ligand.

26 Claims, No Drawings

SOLUBLE ASSAY

This invention relates to an assay for ligands, and more particularly to an assay for ligands having multiple binding sites (at least two determinant sites).

An assay for ligands, and in particular antigens having multiple binding sites is known in the art; for example the so-called 2-site IRMA (immunoradiometric assay). Typically, in such an assay, the ligand in a sample is reacted with solid phase binder therefor, followed by contact with radio labeled binder to provide both labeled binder complexed with the ligand, and remaining free or uncomplexed labeled binder. The amount of ligand present in the sample can be ascertained by determining the amount of labeled binder which has been complexed.

The present invention is directed to an improvement in an assay for multi-site ligands.

In accordance with one aspect of the present invention, there is provided an assay for a ligand having at least two determinant sites (multiple binding sites) wherein a sample containing or suspected of containing the ligand (analyte) is contacted with a first binder, in labeled form, which is specific for the ligand, a second binder different than the first binder which is specific for the ligand and a precipitating binder which is specific for said second binder, with such contacting resulting in a portion of the labeled binder becoming bound to the ligand, and at least a portion of the second binder also becoming bound to the ligand. The complex of ligand bound to both the labeled binder and second binder is precipitated by use of the precipitating binder which is specific for said second binder to separate the complex from the unbound labeled binder. The amount of at least one of the complexed labeled binder and unbound labeled binder (or both) is determined as a measure of the amount of ligand in the sample. Accordingly, by proceeding in accordance with the invention, there is provided a soluble assay for the ligand as compared to a solid phase assay.

In accordance with another aspect of the present invention, there is provided a reagent kit for use in an assay for a ligand having at least two determinant sites, which kit includes a first binder (in labeled form) which is specific for the ligand, a second binder different than the first binder which is specific for the ligand and a precipitating binder which is specific for said second binder.

The kit may further include buffers, standards and the like.

The ligands which are assayed in accordance with the present invention are those which have at least two determinant sites. Thus, for example, the ligands with at least two determinant sites which may be assayed by the invention are generally either polypeptide hormones, polypeptide proteins or non-polypeptide molecules. As representative examples of such antigens, there may be mentioned hTSH (human thyroid stimulating hormones); HCG; insulin; CEA; ferritin; hepatitis associated antigens A and B; alpha-fetoprotein; growth hormone, TSH and the like.

The term different binder includes antibodies raised in different species which are specific to the ligand to be assayed. The binders are different so long as only one of them is bound by the precipitating binder.

In the case where the ligand to be assayed is an antigen, both of the binders used in the assay which are specific to the ligand are generally antibodies, although in some cases, such binder may be a naturally occurring binder. In the case where the ligand to be assayed is an antibody, the binders specific to the ligand are antibodies elicited in response to the antigenic sites of the antibody. As hereinabove indicated, in most cases, the ligand to be assayed is an antigen, whereby the labeled binder for the ligand and the unlabeled binder for the ligand are both antibodies.

As hereinabove indicated, the labeled form of the binder, and the second binder (such second binder is unlabeled) are each bound by determinant sites of the ligand to be assayed. The respective labeled binder and second binder are elicited in two different animal species so that there can be provided a precipitating binder which is specific for only the unlabeled binder (the precipitating binder does not bind to the labeled binder). The labeled binder, and in particular an antibody, is preferably labeled with a suitable radioisotope, as known in the art. As representative examples of such radioisotopes, there may be mentioned radioisotopes of iodine, tritium, cobalt and the like, with radioiodine, and in particular $^{125}$I, being preferred. It is to be understood, however, that the use of other radioisotopes is within the spirit and scope of the invention. Similarly, it is also possible to label the binder with other than a radioisotope; for example, enzyme labeling, fluorescent labeling, etc.

As hereinabove indicated, the other species of antibody is used in an unlabeled form, and such further antibody is also bound to a determinant site of the ligand to be assayed. In this manner, a ligand complex is produced which is comprised of the ligand bound to both the labeled antibody and the unlabeled antibody.

The precipitating binder is one which is capable of being bound to the unlabeled binder of the ligand complex; i.e., the precipitating binder is specific to the unlabeled binder. In most cases, such precipitating binder is a precipitating antibody specific to the unlabeled binder of the complex. Such precipitating antibody may be produced by procedures known in the art such as, for example, eliciting the precipitating antibody in response to the unlabeled antibody. The precipitating antibody should be elicited in an animal species different than the animal species in which the first binder is elicited. Thus, for example, if the unlabeled antibody is elicited by the use of rabbits, the precipitating antibody may be produced by injecting goats with the produced rabbit antiserum or normal rabbit immunoglobulin. Thus, the precipitating antibody is one which reacts with the antigenic sites of the unlabeled antibody. The precipitating binder, preferably an antibody, is one which is capable of crosslinking at least two different molecules of the unlabeled binder to produce macromolecular structures which precipitate.

In performing the assay, the sample containing or suspected of containing the ligand having at least two determinant sites is incubated with a first binder, in labeled form, specific to the ligand to be assayed, and a second binder, which is unlabeled, and which is specific to the ligand to be assayed, with the labeled form of the first antibody being employed in an amount which is in a well-defined relationship to the unlabeled antibody. The first binder in labeled form, and the second binder, which is unlabeled, may be added to the sample simultaneously or sequentially.

Thus, for example, when determining an antigen in a sample with measurable amounts of antigen, both the labeled and unlabeled binder may be added simultaneously to the sample, and after a predetermined incubation (time and temperature dependent) the precipitating binder is added followed by separation of the precipitate from the supernatent; e.g., by centrifugation.

If the sample is suspected of containing high antigen concentrations, the labeled antibody may be initially reacted with the sample, followed by incubation with an excess of unlabeled antibody and then by addition of precipitating antibody.

As a result of such contact, a portion of the first binder, in labeled form, becomes bound to the ligand to be assayed, and another portion of such first binder may remain free; i.e., is not bound to the ligand. The second binder, which is unlabeled, also becomes bound to the ligand, and in accordance with the present invention, the complex comprised of the ligand to be assayed and the two binders is separated from the unbound first binder, in labeled form, by use of precipitating binder specific for the second binder, and which precipitating binder, when bound to the complex, forms a precipitate which can be separated from the sample. Such precipitate is a complex comprised of the precipitating binder, unlabeled second binder, ligand to be assayed and labeled first binder. Under some circumstances the precipitating binder and the labeled binder can be premixed. The addition of this premixed reagent, followed by incubation with the unlabeled binder, would then trigger the formation of the insoluble complex.

The precipitate is then separated from the supernatant fluid, which supernatant fluid includes the unbound first binder in labeled form, and the amount of labeled first binder which is bound in the complex increases with an increase in the concentration of the ligand to be assayed in the sample. Similarly, the amount of first binder, in labeled form, which is unbound, and which remains in the supernatant fluid, decreases with an increase in the concentration of the ligand to be assayed in the sample. By ascertaining the amount of at least one of the complex and free first binder, in labeled form, it is possible to measure the amount of ligand present in the sample. As known in the art, a quantitative determination can be made by comparing the determined amount to a standard curve, which was prepared from use of various samples having known concentrations to the ligand to be assayed.

As should be apparent, if the sample does not contain a measurable amount of ligand (analyte) the precipitate will not include any labeled binder; i.e., no complex is formed and the precipitating binder precipitates the unlabeled second binder.

In accordance with another aspect of the invention, there is provided a suitable reagent kit or package for accomplishing the assay, which includes as principle components in suitable reagent containers: (a) a first binder, in labeled form specific for the ligand to be assayed, which binder is preferably an antibody, with such antibody preferably being labeled with a radioisotope,; and in particular, radioiodine; (b) a second binder different than the first binder specific for the ligand to be assayed, which second binder is unlabeled, and is preferably an antibody; and (c) a precipitating binder specific for the second binder which is capable of precipitating a complex comprised of the ligand to be assayed, first binder and second binder, with such precipitating binder also preferably being an antibody. Such components or premixed components, where applicable, are included in the reagent kit or package in separate containers; for example, vials. It is possible to provide the first and second binders or the first binder and the precipitating binder in a single container or vial. The first and second binders are in unsupported form. The reagent kit or package may also include other components such as standards of the ligand to be assayed; i.e., ligand samples having known concentrations of the ligand to be assayed, buffers, and the like.

The invention will be further described with respect to the following examples; however, the scope of the invention is not to be limited thereby:

I. REAGENTS

A. Human Liver Ferritin Standards. Prepared from human liver ferritin purified using a modification of the procedure by S. Granick in the Journal of Biological Chemistry. 146 (1942).

B. Anti-Human Ferritin (Goat). Antiserum to human ferritin raised in goats by standard hyperimmunization protocols using complete Freund's adjuvant (CFA). Optimal dilution of antiserum prepared in buffered solution.

C. $^{125}$I-Anti-Human Ferritin (Rabbit). Antiserum to human ferritin raised in rabbits by standard hyperimmunization protocols with CFA and subsequently purified by affinity chromatography procedures prior to labeling with $^{125}$I. Working reagent is diluted in a stabilizing buffered solution.

D. Anti-Goat Gammaglobulins (Rabbit). Antiserum to goat gamma globulins raised in rabbits by standard hyperimmunization protocols using CFA. Optimal dilution prepared in buffered solution.

E. Dilution buffer for cold or untagged antibody and for precipitating antibody:
  0.05 M $Na_2 HPO_4$ - $Na H_2 PO_4$ in 0.5% (weight-/volume) Bovine serum Albumin, containing 0.1% Sodium Azide, adjusted to pH 7.5 with 1N HCl or 1N NaOH F. Dilution buffer for tagged or radioactive antibody:
  0.1M $Na_2 HPO_4$ - $Na H_2 PO_4$ in 5% Bovine Serum Albumin containing 0.1% Sodium Azide adjusted to pH 7.5 with 1N HCl or 1N NaOH.

G. The dilution of the antibodies in the above mentioned buffers follows.
  (1) Cold Antibody: 1:1,000 to 1:10,000 dilution depending on titer.
  (2) Tagged Antibody: Depending on specific activity of iodinated product — to yield a concentration of approximately 100,000 CPM/per tube.
  (3) Precipitating Antibody: Depending on titer, use undilute to a 1:20 dilution.

II. PROCEDURE

1. Add 25 uL of STANDARD or UNKNOWN to 12 ×75 mm glass or plastic test tubes.

2. Add 100 uL of $^{125}$I-Anti-Human Ferritin (Rabbit). Mix.

3. Add 100 uL of Anti-Human Ferritin (Goat). Mix. (Alternately, $^{125}$I-Anti-Human Ferritin (Rabbit) and Anti-Human Ferritin (Goat) reagents can be premixed and 200 uL of a single reagent added to all tubes).

4. Incubate 30 minutes at 37° C.

5. Add 50 uL of Anti-Goat Gammaglobulins (rabbit). Mix. (Alternately, $^{125}$I-Anti-Human Ferritin (Rabbit) and Anti-Goat Gammaglobulin (Rabbit) can be premixed and 200 uL of a single reagent added to all tubes. Addition of this reagent would then be followed by the step of addition of the unlabeled binder.)

6. Incubate 15 minutes at 37° C.
7. Add approximately 4 mL of normal saline to each tube.
8. Centrifuge for 10 to 15 minutes at 1000 RCF.
9. Decant all tubes and blot dry.
10. Count the precipitates.

The present invention is particularly advantageous in that it does not require a binder to be coupled to an insoluble support as in prior art processes. As a result of eliminating the necessity to support the binder, reagents are more easily standardized on a lot to lot basis. In addition, the assay is highly sensitive (estimated at 6 pg/ml for ferritin), and the concentration of binder can be adjusted to accomplish a wide range of values or to use a small sample size. Furthermore, as a result of separation by precipitation, with the precipitate being easily separated by filtration, the system may be easily automated.

In addition, the assay may be accomplished in short times; for example, as short as 30 minutes or less.

These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

We claim:

1. A process for the assay of a ligand having at least two determinant sites, comprising:
    contacting in solution a sample containing said ligand with a first unsupported binder, in labeled form, which is specific for the ligand, said first binder being a member selected from the group consisting of a first antibody and a first naturally occurring binder, a second unsupported binder, which is unlabeled, and which is specific for the ligand, said second binder being a member selected from the group consisting of a second antibody and a second naturally occurring binder, said first and second antibody being raised in different animal species, and said first and second naturally occurring binders being different substances, and an unsupported soluble precipitating binder specific for said second binder, said contacting binding a portion of the first binder and at least a portion of the second binder to the ligand and precipitating a complex comprising the precipitating binder and ligand bound to both the first binder and second binder; and determining the amount of first binder in at least one of the solution and the complex as a measure of the ligand in the sample.

2. The process of claim 1 wherein the first and second binders are each antibodies.

3. The process of claim 2 wherein the ligand is an antigen.

4. The process of claim 3 wherein the ligand is selected from the group consisting of HCG, insulin, human thyroid stimulating hormone, ferritin, hepatitis associated antigens A and B, alpha-fetoprotein, thyroid stimulating hormone and CEA.

5. The process of claim 2 wherein the precipitating binder is a precipitating antibody which reacts with the antigenic sites of the second binder.

6. The process of claim 5 wherein the first antibody is labeled with a radioisotope.

7. The process of claim 6 wherein the radioisotope is a radioisotope of iodine.

8. The process of claim 7 wherein the ligand is TSH.

9. The process of claim 7 wherein the ligand is ferritin.

10. The process of claim 7 wherein the ligand is hepatitis associated antigen.

11. The process of claim 1 wherein the first and second binders are sequentially contacted with the sample.

12. The process of claim 1 wherein the first and second binders are simultaneously contacted with the sample.

13. The process of claim 1 wherein the first and precipitating binders are simultaneously contacted with the second binder.

14. A reagent kit for the assay of a ligand having at least two determinant sites, comprising:
    in reagent containers, an unsupported first binder, in labeled form, specific for said ligand, said first binder being a member selected from the group consisting of a first antibody and a first naturally occurring binder;
    an unsupported second binder which is unlabeled and which is specific for the ligand to be assayed, said second binder being a member selected from the group consisting of a second antibody and a second naturally occurring binder, said first and second anitbody being antibodies raised in different animal species, and said first and second naturally occurring binders being different substances; and
    an unsupported soluble precipitating binder specific for said second binder.

15. The reagent kit of claim 14 wherein the first and second binders are each antibodies.

16. The reagant kit of claim 15 wherein the precipitating binder is a precipitating antibody which reacts with the antigenic sites of the second binder.

17. The reagant kit of claim 16 wherein the first antibody is labeled with a radioisotope.

18. The reagant kit of claim 17 wherein the radioisotope is a radioisotope of iodine.

19. The reagant kit of claim 18 wherein the ligand is TSH.

20. The reagant kit of claim 18 wherein the ligand is ferritin.

21. The reagant kit of claim 18 wherein the ligand is hepatitis associated antigen.

22. The reagent kit of claim 14 wherein the first and second binders are in a single reagent container.

23. The reagent kit of claim 14 wherein the first and second binders are in separate reagent containers.

24. An assay for human ferritin, comprising:
    contacting a serum sample containing human ferritin with a tracer comprising unsupported ferritin antibody labeled with a radioactive isotope, unsupported unlabeled ferritin antiserum, said labeled antibody and unlabeled antiserum being raised in different animal species, and an unsupported soluble precipitating antibody specific for the unlabeled ferritin antiserum, said contacting binding a portion of the tracer and at least a portion of the ferritin antiserum to the ferritin in the sample and precipitating a complex comprising the precipitating antibody and ferritin bound to both the tracer and unlabeled ferritin antiserum; and determining the amount of tracer in at least one of the solution and the complex as a measure of ferritin in the serum.

25. The process of claim 24 wherein the solution and complex are separated from each other prior to said determining.

26. The assay of claim 25 wherein the ferritin antibody is raised in rabbit, the ferritin antiserum is raised in goat, and the precipitating antibody is rabbit antiserum to goat IgG.

* * * * *